United States Patent
Fucci et al.

(10) Patent No.: US 6,346,109 B1
(45) Date of Patent: Feb. 12, 2002

(54) CANNULATED TISSUE ANCHOR SYSTEM

(75) Inventors: Joseph Fucci, Palm Harbor; Robert C. Hackett, Tampa; T. Dan Moore, St. Petersburg; Mark A. Bellafiore, Clearwater, all of FL (US)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 09/591,376

(22) Filed: Jun. 9, 2000

Related U.S. Application Data

(62) Division of application No. 09/141,175, filed on Aug. 26, 1998, now Pat. No. 6,146,387.

(51) Int. Cl.⁷ .............................................. A61B 17/56
(52) U.S. Cl. ......................... 606/104; 606/72; 206/339
(58) Field of Search ........................ 606/104, 72, 139, 606/232; 206/206, 571, 338, 339, 438, 562, 563, 370, 340, 341, 365, 364, 470, 63.3

(56) References Cited

U.S. PATENT DOCUMENTS

| | | |
|---|---|---|
| 170,190 A | 11/1875 | Pratt |
| 204,913 A | 6/1878 | Pratt |
| 362,843 A | 5/1887 | Kerrison, Jr. |
| 368,687 A | 8/1887 | Rogers |
| 816,026 A | 3/1906 | Meier |
| 1,153,450 A | 9/1915 | Schaff |
| 1,321,011 A | 11/1919 | Cottes |
| 1,848,318 A | 3/1932 | Ciampi |
| 2,020,062 A | 11/1935 | Jackson |
| 2,065,659 A | 12/1936 | Cullen |
| 2,243,717 A | 5/1941 | Moreira |
| 2,248,054 A | 7/1941 | Becker |
| 2,267,925 A | 12/1941 | Johnston |
| 2,413,142 A | 12/1946 | Jones et al. |
| 2,631,584 A | 3/1953 | Purificato |
| 2,725,053 A | 11/1955 | Bambara et al. |
| 2,779,083 A | 1/1957 | Eaton |

(List continued on next page.)

FOREIGN PATENT DOCUMENTS

| | | |
|---|---|---|
| EP | 0 770 354 | 10/1996 |
| JP | 54-11158 | 3/1977 |
| JP | 61-40418 | 11/1983 |
| JP | 60-25213 | 10/1997 |
| RU | 196243 | 11/1964 |

OTHER PUBLICATIONS

Article Entitled "R&D and Design Play Important Role in Development of New Biopsy Forceps", Medical Product Manufacturing News, Oct. 97 Two Pages.

Article Entitled "Boat–Nail Fixation of Tendons and Ligaments to Cancellous Bone" Journal of Bone & Joint Surgery, Oct. 1956 Three Pages.

*Primary Examiner*—David O. Reip
*Assistant Examiner*—Julian W. Woo
(74) *Attorney, Agent, or Firm*—Gene Warzecha

(57) ABSTRACT

A system for inserting a cannulated tissue anchor during endoscopic surgical procedures. The system incorporates an elongated generally cylindrical tissue anchor having a plurality of barbs outwardly extending from its body and a transverse head situated at its proximal end. The head is elongated along a major axis which is misaligned relative to the rows of barbs on the body of the tissue anchor in order to enhance retention of the anchor within selected tissue. The anchor may be inserted during an endoscopic surgical procedure by a single-handed operation utilizing an instrument having a longitudinally slidable needle for guiding the anchor into place and a longitudinally slidable push rod for pushing the anchor along the needle. The system incorporates a package/loading device to facilitate the assembly of a cannulated tissue anchor with the inserter, the package/loading device being provided with a means for guiding the inserter needle through the axial bore of the tissue anchor.

6 Claims, 19 Drawing Sheets

U.S. PATENT DOCUMENTS

| | | | |
|---|---|---|---|
| 3,003,155 A | 10/1961 | Mielzynski et al. | |
| 3,123,077 A | 3/1964 | Alcamo | |
| 3,166,072 A | 1/1965 | Sullivan, Jr. | |
| 3,399,432 A | 9/1968 | Merser | |
| 3,470,834 A | 10/1969 | Bone | |
| 3,699,969 A | 10/1972 | Allen | |
| 3,716,058 A | 2/1973 | Tanner, Jr. | |
| 3,848,080 A | 11/1974 | Schmidt | |
| 3,862,684 A * | 1/1975 | Schmitt | 206/438 |
| 3,892,232 A | 7/1975 | Neufeld | |
| 3,946,740 A | 3/1976 | Bassett | |
| 4,006,747 A | 2/1977 | Kronenthal et al. | |
| 4,007,732 A | 2/1977 | Kvavle et al. | |
| 4,060,089 A | 11/1977 | Schreiber | |
| 4,235,238 A | 11/1980 | Ogiu et al. | |
| 4,244,370 A | 1/1981 | Furlow et al. | |
| 4,259,959 A | 4/1981 | Walker | |
| 4,261,351 A | 4/1981 | Scherfel | |
| 4,263,903 A | 4/1981 | Griggs | |
| 4,316,469 A | 2/1982 | Kapitanov | |
| 4,383,527 A | 5/1983 | Asnis et al. | |
| 4,409,974 A | 10/1983 | Freedland | |
| 4,462,395 A | 7/1984 | Johnson | |
| 4,493,323 A | 1/1985 | Albright et al. | |
| 4,635,637 A | 1/1987 | Schreiber | |
| 4,884,572 A | 12/1989 | Bays et al. | |
| 4,895,148 A | 1/1990 | Bays et al. | |
| 4,924,865 A | 5/1990 | Bays et al. | |
| 4,968,317 A | 11/1990 | Tormala et al. | |
| 4,976,715 A | 12/1990 | Bays et al. | |
| 5,031,768 A * | 7/1991 | Fischer | 206/438 |
| 5,144,942 A * | 9/1992 | Decarie et al. | 206/571 |
| 5,466,243 A | 11/1995 | Schmieding et al. | |
| 5,562,704 A | 10/1996 | Tamminmaki | |
| 5,569,252 A | 10/1996 | Justin et al. | |
| 5,715,942 A * | 2/1998 | Li et al. | 206/339 |
| 5,730,744 A | 3/1998 | Justin et al. | |
| 5,782,862 A | 7/1998 | Bonutti | |
| 5,868,250 A * | 2/1999 | Brackett | 206/438 |
| 5,928,252 A | 7/1999 | Steadman et al. | |

* cited by examiner

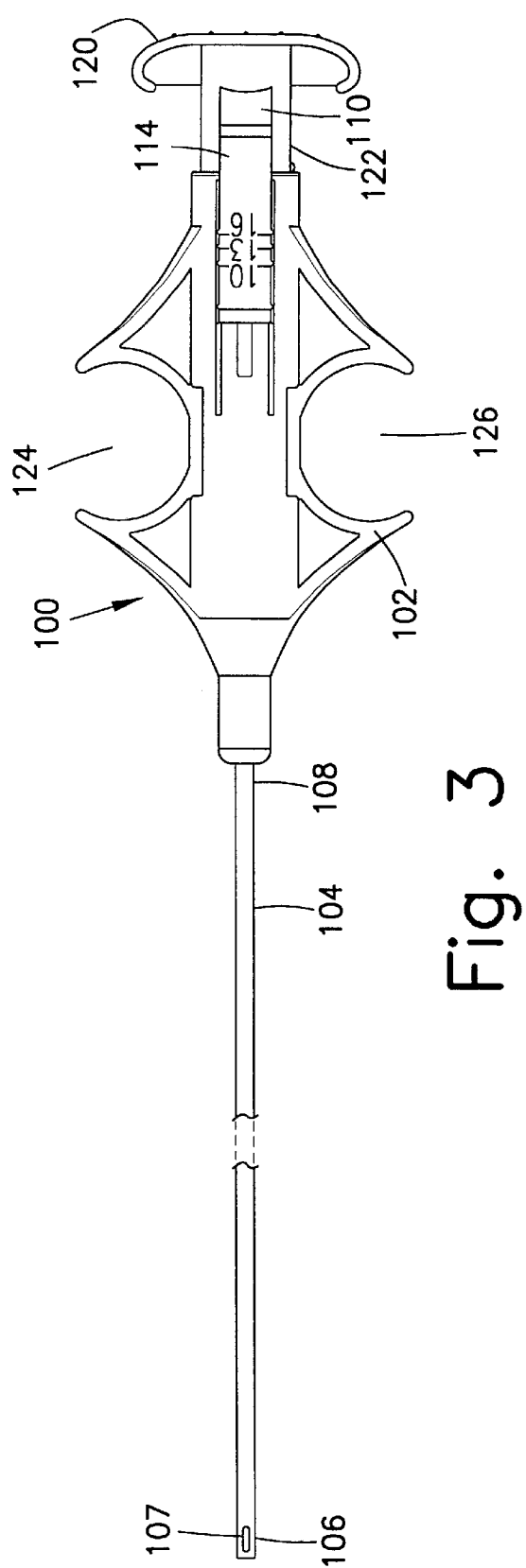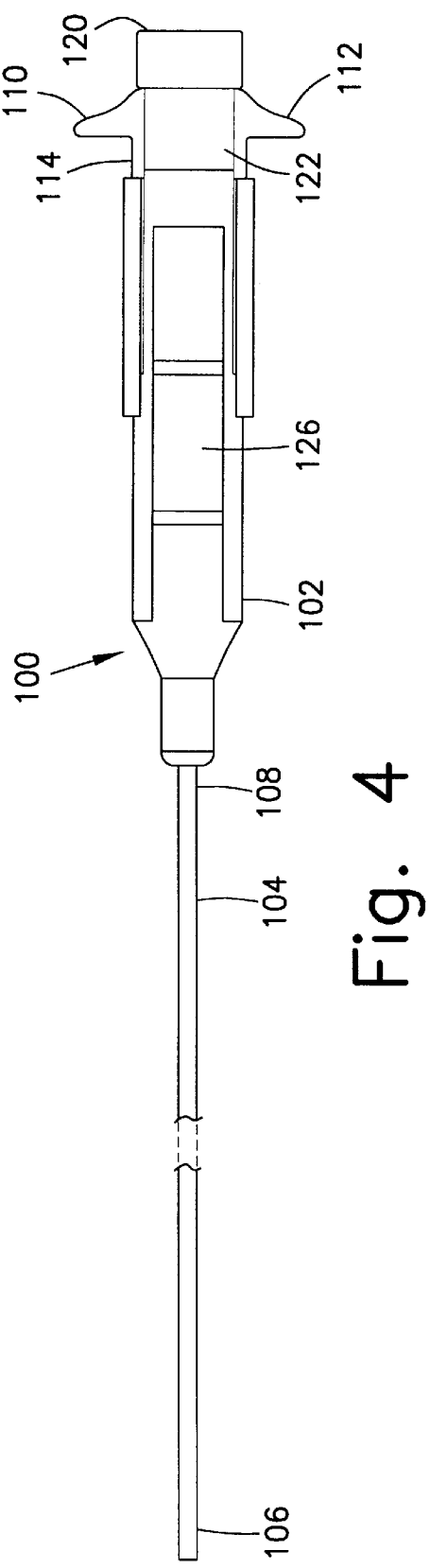

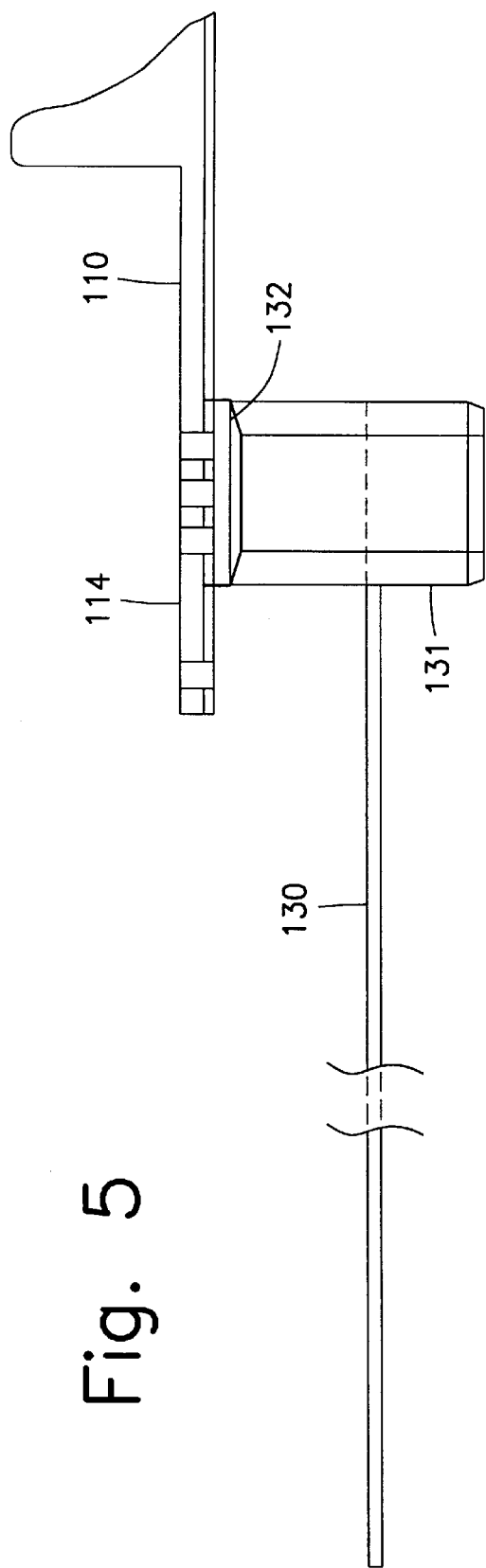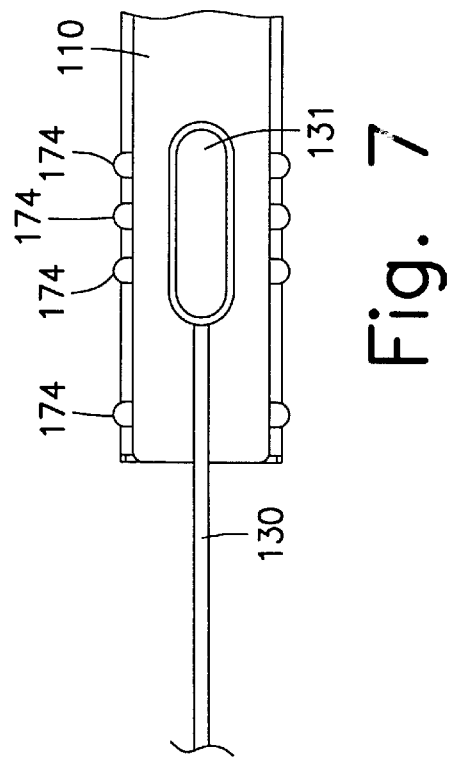

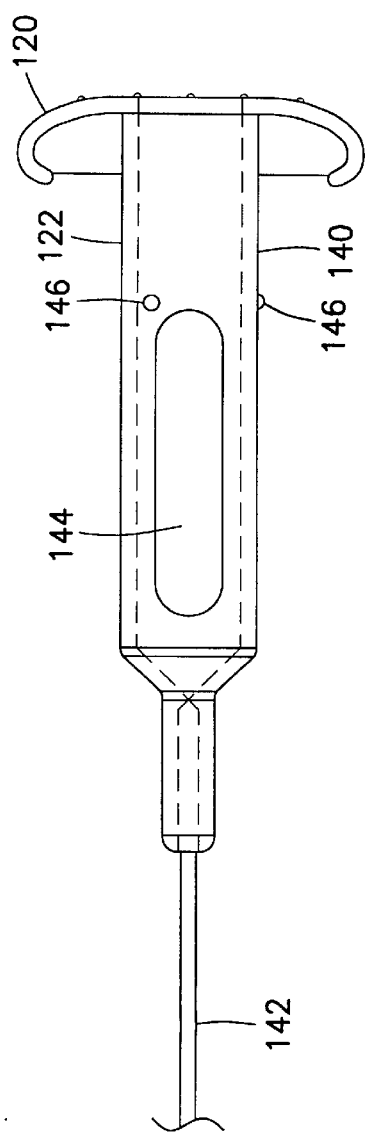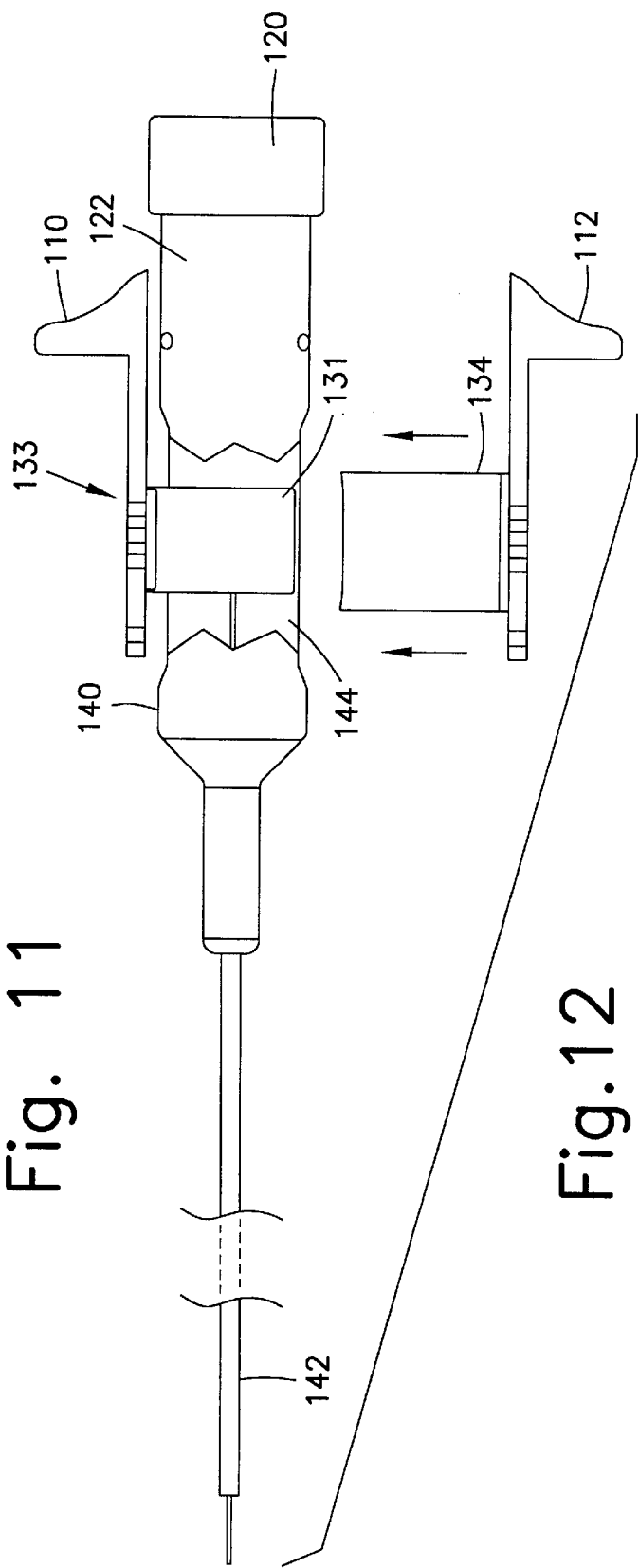
Fig. 11
Fig. 12

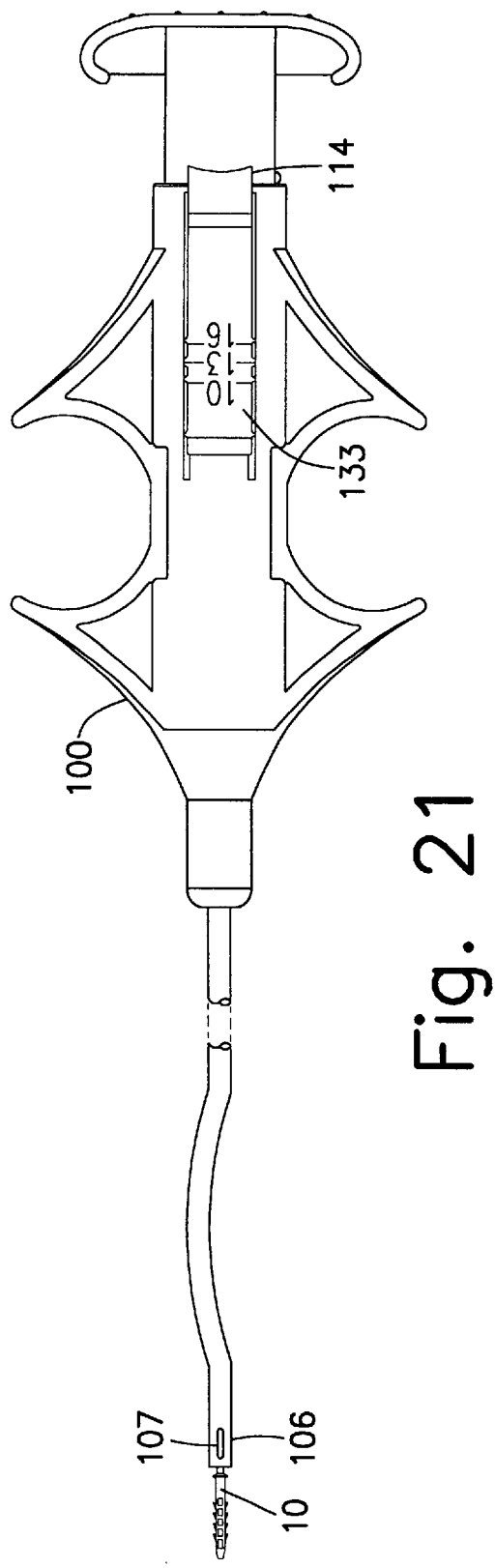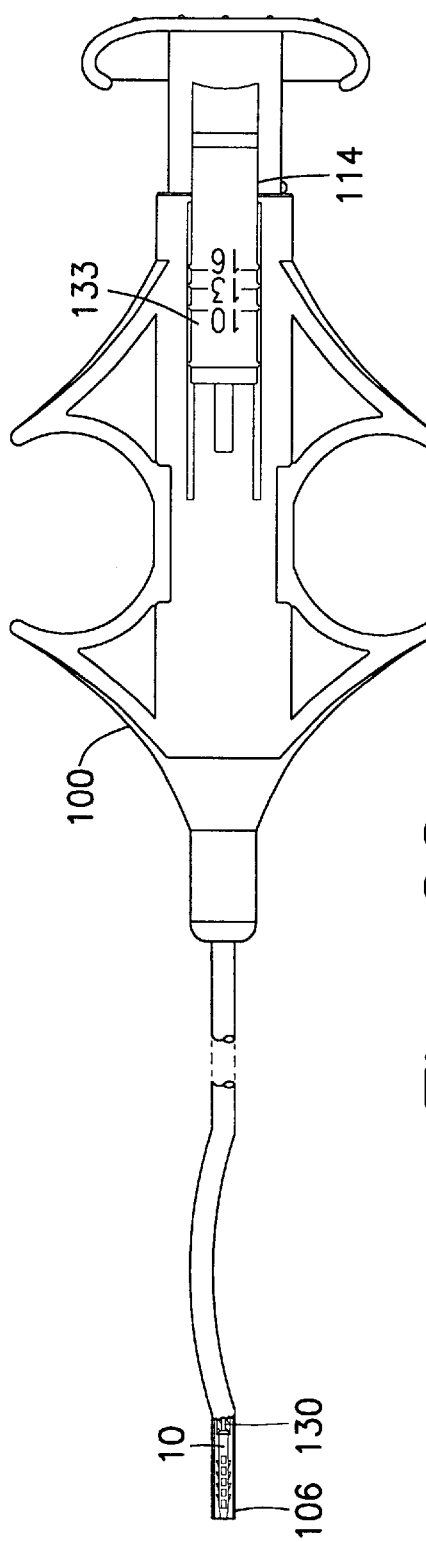
Fig. 21
Fig. 22

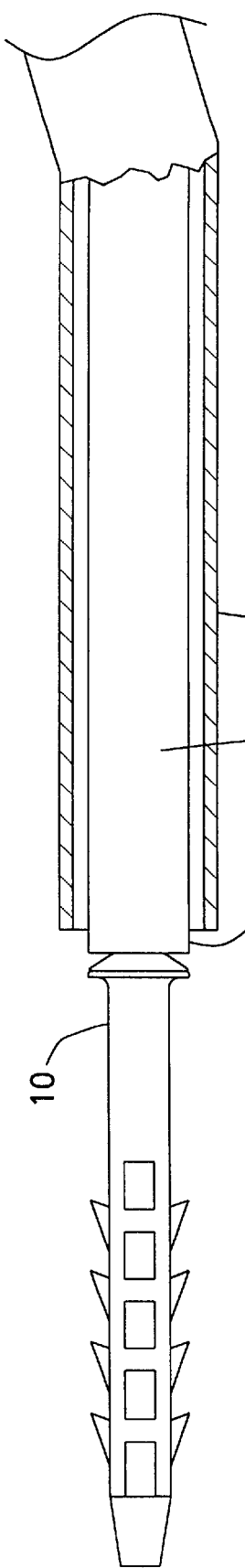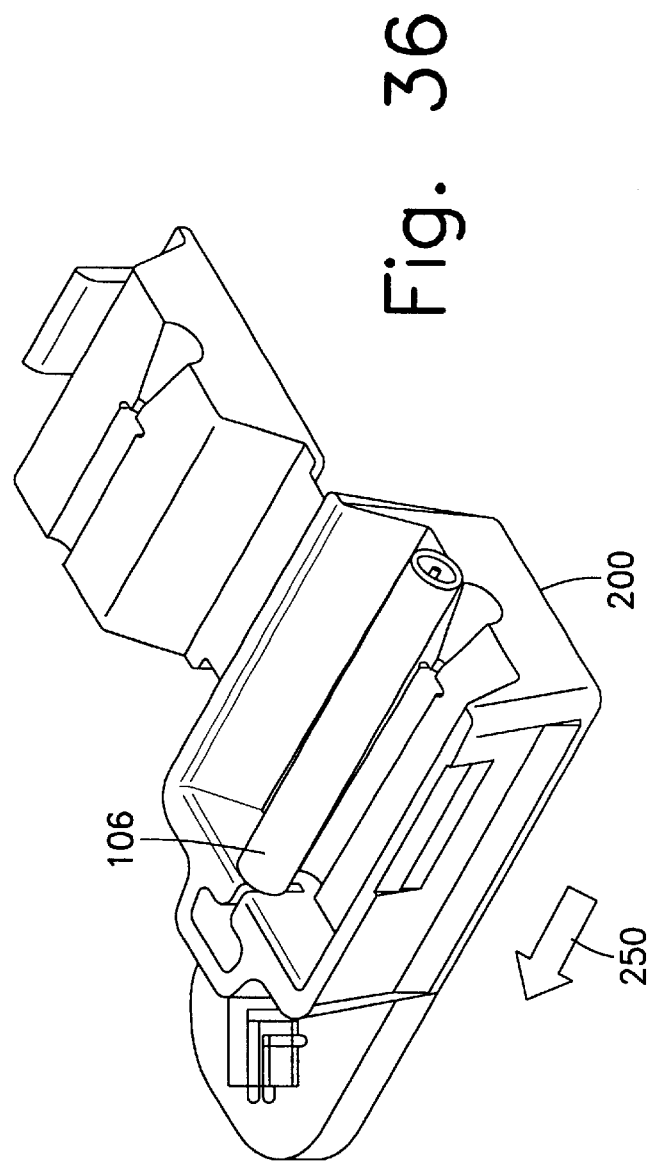

CANNULATED TISSUE ANCHOR SYSTEM

This is a divisional application of application Ser. No. 09/141,175, filed Aug. 26, 1998, now U.S. Pat. No. 6,146,387.

BACKGROUND OF THE INVENTION

1. Field of the Invention

The invention relates to implant devices and instruments used to repair body tissue. In particular, the invention relates to an implant device, instruments and methods for repairing body tissue during endoscopic surgical procedures. Still more particularly, the invention relates to implant devices, instruments and methods for repairing meniscal tissue during arthroscopic surgery of the knee.

2. Description of the Prior Art

Implant devices for repairing body tissue are known in the prior art. While such devices may be classified into several categories, the present invention is related to elongated devices having transversely extending barbs or projections which assist in retaining the implant in place within a tissue defect (e.g. a tear) to hold body tissue in close approximation during the healing process.

One such known device is described in U.S. Pat. No. 4,873,976 (Schrieber). This device comprises a solid elongated shaft having a plurality of transversely extending projections, a pointed tip and a transverse circular head at its proximal end.

Other similar devices are disclosed in U.S. Pat. Nos. 4,884,572; 4,895,148; 4,924,865; and 4,976,715 all issued to Bays et al. The devices disclosed in these Bays et al. patents primarily differ from the Schrieber device in that they are cannulated. The Bays et al. patents are assigned to the assignee hereof and, along with Schrieber, are incorporated by reference herein.

All of the above described elongated devices are arrow-like and are designed to be inserted or pushed into tissue to be repaired. The devices are sometimes referred to as "tissue anchors" because they hold tissue together during healing. While these devices are intended to be used during arthroscopic or more generally endoscopic procedures, that very fact makes the insertion sometimes difficult. It is known to use elongated cannulas to guide the implants into position and smaller push rods to push them in. In the Schrieber type device, the implant is pushed through a cannula with an elongated pusher sized to be slidingly received within the cannula. With devices such as those disclosed in the Bays et al. patents the implant device is secured to the distal tip of a holding device and pushed into place, with or without the use of a guiding cannula.

All such arrow-like implant devices must not only enter tissue easily, but must resist migration once situated in place. Consequently, it is an object of this invention to provide a tissue anchor which has barbs to facilitate insertion and has a head design to minimize distal migration.

It is desirable to simplify the insertion process for these types of push-in arrow-like implant devices. It is also desirable to make such modifications to prior art arrow-like implant devices and systems as may improve their use and performance during and after (i.e. during healing when retention within tissue is important).

Accordingly, it is a further object of this invention to develop a tissue repair system incorporating a cannulated push-in implant or tissue anchor device, preferably bioabsorbable, and a simplified insertion apparatus, preferably operable by one hand.

It is also generally an object of this invention to provide a tissue anchor inserting device and method for guiding and inserting a cannulated tissue anchor into position at a surgical site.

It is another object of this invention to provide an elongated inserting device for receiving therein a cannulated tissue anchor, preferably at its distal end.

It is still another object of this invention to provide an elongated inserting device suitable for endoscopic procedures and capable of being operated from its proximal end.

It is also an object of this invention to provide a tissue anchor inserting system which facilitates the assembly of an inserting device with a cannulated tissue anchor.

It is yet another object of this invention to provide such a system with a holder for retaining a tissue anchor to facilitate such assembly.

SUMMARY OF THE INVENTION

These and other objects are accomplished by the preferred embodiment of the system disclosed herein which comprises a tissue anchor component, an inserter component and a package component. The tissue anchor component is a device comprising an elongated shaft having a proximal end, a distal end and a longitudinally extending bore therethrough. A plurality of barbs is longitudinally spaced along the shaft and the barbs are tapered in a distal direction to facilitate distal movement of the shaft through tissue material. The barbs are aligned in at least one row (preferably four rows) on the external surface of the shaft and a transversely extending head is situated at the proximal end of the shaft. The head has an aperture aligned with the bore and is generally elongated along a major axis which is misaligned relative to at least one of the rows of barbs.

The invention also resides in a tissue anchor inserter component and method for using the inserter with a cannulated tissue anchor. The inserter comprises a housing, a first elongated tubular shaft extending distally from the housing, the shaft having an axially aligned bore therethrough and an elongated needle adapted to be slidably received within the bore. The shaft is adapted to receive a cannulated tissue anchor while the needle is adapted to be received in the bore of the anchor. A trigger means is provided for moving the distal end of the needle between a first, retracted position, in which the needle is maintained within the bore, and a second, extended position, in which the needle is extended distally, beyond the bore. A pusher rod for pushing the anchor out of the device is adapted to be slidably received within the bore and moved between a first, retracted position, in which the distal end of the pusher rod is maintained within the bore of the shaft, and a second, extended position, in which the distal end of the pusher rod is adjacent the distal end of the shaft.

The inserter component is used to perform the method of inserting a cannulated tissue anchor into tissue to be treated at a surgical site. The method comprises the steps of providing a cannulated tissue anchor and providing a tissue anchor inserter as described above. The method further comprises providing the tubular shaft with a receiving chamber, for slidably receiving the needle and the tissue anchor, and a pusher means for engaging the tissue anchor to push it out of the receiving chamber. The needle is then extended distally from the receiving chamber, inserted into the bore of the tissue anchor and then retracted with the tissue anchor into the receiving chamber. The surgical site at which the tissue anchor is to be placed is located and the needle is extended from the receiving chamber into tissue at the surgical site. The pusher means is advanced distally to push the tissue anchor distally along the extended needle and into the surgical tissue. The procedure is completed by removing the needle from the tissue.

The invention also resides in a combination package and loading component which is a device for retaining a cannulated tissue anchor and facilitating its assembly with the above described inserter. The package comprises a base and a funnel means, the base having a first surface for receiving a cannulated tissue anchor thereon in predetermined orientation and the funnel means for being aligned with the bore of the tissue anchor to facilitate insertion of the inserter needle into the anchor. The package further comprises a releasable holding means having a second surface for holding the tissue anchor in alignment with the funnel until the assembly of the anchor with the inserter has been completed.

BRIEF DESCRIPTION OF THE DRAWINGS

FIG. 3 is a plan view of an inserting instrument for use with the implant device shown in FIG. 1.

FIG. 4 is a side elevational view of FIG. 3.

FIG. 5 is a side elevation view of a portion of the needle means used in the instrument of FIG. 3.

FIG. 6 is a right side view of FIG. 5.

FIG. 7 is a partial bottom plan view of FIG. 5.

FIG. 11 is a plan view of the pusher means used in the instrument of FIG. 3.

FIG. 12 is a side elevation view of a partially assembled inserting instrument showing the needle means and the pusher means.

FIG. 21 shows the inserting instrument of FIG. 20 showing an implant device in place at the distal tip of the instrument.

FIG. 22 shows the instrument of FIG. 21, partially in cross-section, showing the implant device retracted into the body of the inserting instrument.

FIG. 27 is a close-up of the distal end of FIG. 26.

FIGS. 32 through 36 are various views of the package/loading device shown in FIGS. 28 through 31 showing various steps in the process of loading a cannulated tissue anchor onto an associated insertion device.

DESCRIPTION OF THE PREFERRED EMBODIMENT

Figures 1, 2:
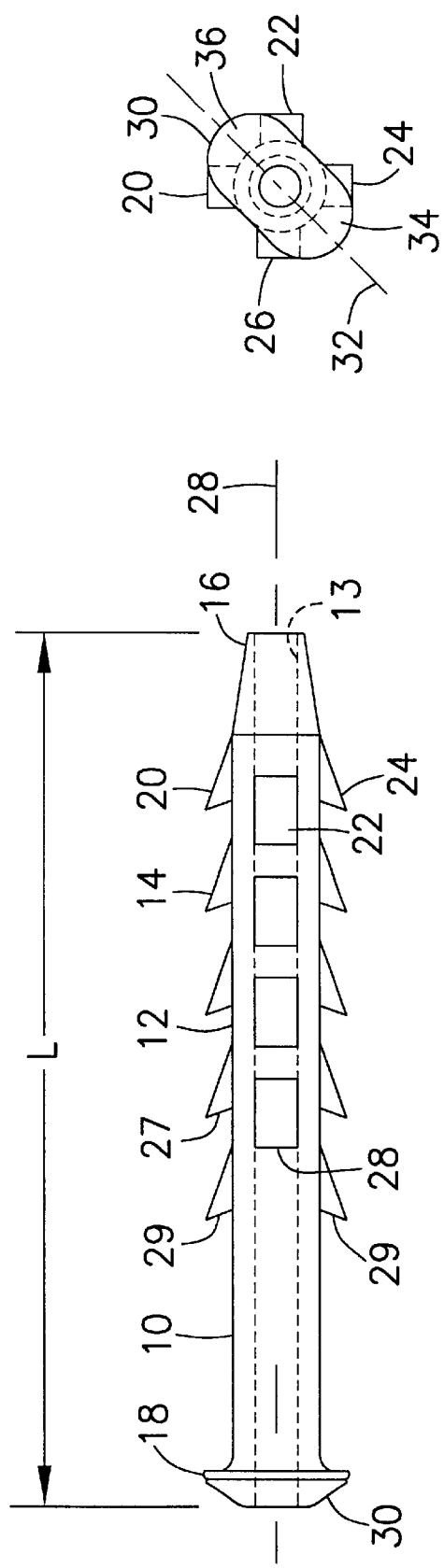
FIG. 1 is a side elevational view of a cannulated implant device constructed in accordance with the principles of this invention.
FIG. 2 is a left end view thereof showing the head in phantom.
Figure 10:
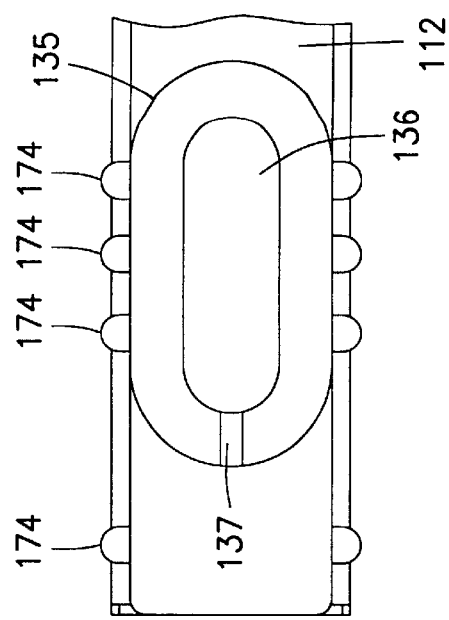
FIG. 10 is a partial top plan view of FIG. 8.
Figure 9:
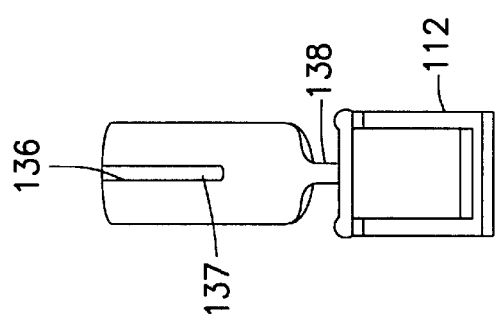
FIG. 9 is a left side view of FIG. 8.
Figure 8:
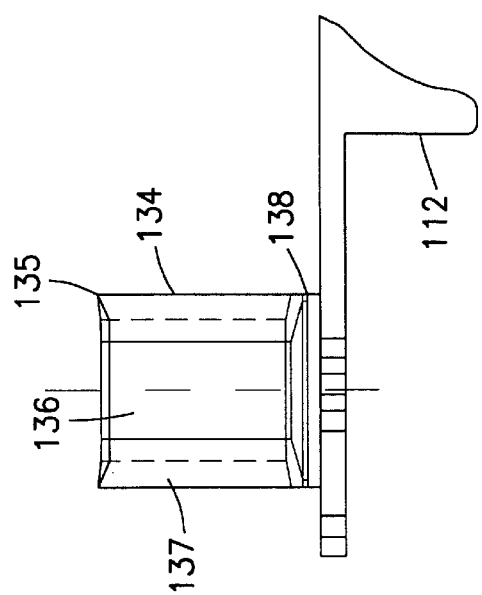
FIG. 8 is a side elevation view of the remaining portion of the needle means, this portion intended to be assembled with the portion shown in FIG. 5.

Referring now to FIGS. 1 and 2 there is shown a cannulated tissue anchor 10 constructed in accordance with the principles of this invention. While anchor 10 is generally constructed in accordance with the teachings of the aforementioned Bays et al. patents, it will be noted that anchor 10 comprises some improvements over all known prior art tissue anchors. Thus, anchor 10 comprises an elongated shaft 12 having an axial bore 13 and a plurality of barbs 14 situated on its external surface and extending between a distal end 16 and a proximal end 18. The barbs are arranged in four linear rows 20, 22, 24 and 26 with rows 20 and 24 having an equal number of barbs in each row and rows 22 and 26 having a lesser number of barbs in each row. The barbs in adjacent rows are longitudinally staggered to enable the tissue anchor to resist rotation about its axis 28. The anchor may be made in various lengths and diameters with various numbers of barbs and with various lengths of smooth, barb-free shafts between the proximal most barbs 29 and proximal end 18. In the preferred embodiment, all rows have three barbs each if the anchor length L is 10 mm. If the anchor length L is 13 mm or 16 mm, rows 20 and 24 each have five barbs and rows 22 and 26 each have four barbs (as shown in FIG. 1). The distal-most barbs in all cases are situated at the same distance from distal end 16.

In the preferred embodiment, the barbs on opposing rows 20 and 24 are undercut on their proximally facing side 27 at an angle of approximately 21° facing proximally. The barbs on opposing rows 22 and 26 are not undercut and their proximally facing surfaces 28 are perpendicular to axis 28. As will be understood by those skilled in the art, this arrangement permits the anchor to be molded in a two-part mold with a parting line through rows 20 and 24. The undercut enhances the holding strength of the anchor by enabling tissue to "flow" back behind the undercut barbs as the anchor is pushed into place.

Anchor 10 further comprises a head 30 at its proximal end 18. In the preferred embodiment, head 30 is a generally flat oval structure having a major axis 32 which is angled relative to the plane of rows 20 and 24 as best seen in FIG. 2. This intentional misalignment of the axis of head 32 enables it to abut tissue in the areas adjacent to the distally facing sides of portions 34 and 36 of the head. It will be understood that as the barb rows 20, 22, 24 and 26 are pushed into tissue to be treated at the surgical site, the tissue is necessarily pushed aside or slightly deformed in the areas adjacent the barbs and along the lines of the barbs. If the head axis 32 were to be aligned in the plane of two diametrically opposed rows of barbs, for example, the head may have a tendency to migrate distally along the tissue defects created by the barb rows. The intentional misalignment of the axis of the head prevents the distal advancement of the barb because the head lies adjacent "virgin" tissue which is not subject to deformation by the barb rows. Thus, it will be understood that the particular shape and orientation of head 30 enables the profile of the head to be minimized while also minimizing the possible migration of the tissue anchor at or from the surgical site. This beneficial orientation of the major axis of the head would also apply to tissue anchors in which the barbs might be arranged in helical rows.

Figure 20:
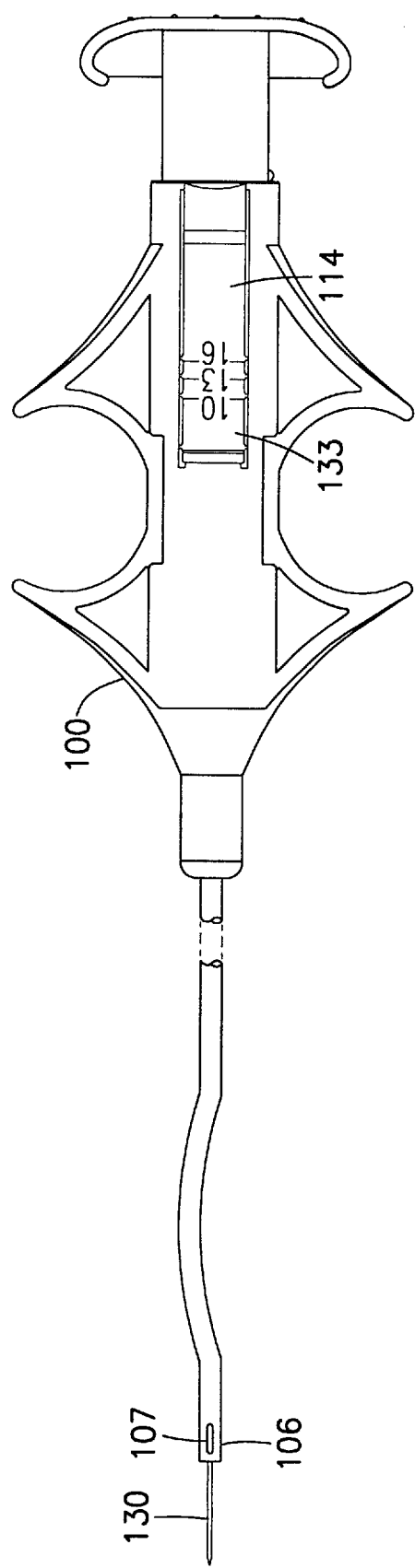
FIG. 20 is an alternate embodiment of the instrument shown in FIG. 3 showing the instrument during one stage of the process for using the instrument with an implant device such as that shown in FIG. 1.
Figure 23:
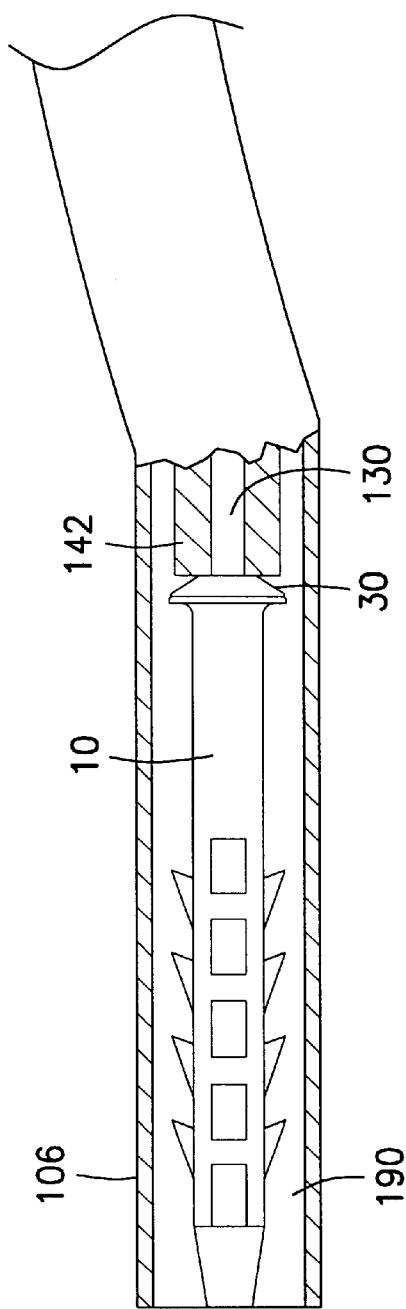
FIG. 23 shows a close-up of the distal tip of the instrument of FIG. 22.

Referring now to FIGS. 3 through 12, there is described a tissue anchor inserter system for inserting a cannulated tissue anchor (such as anchor 10) and the method for using same. While the inserter shown in FIGS. 3 and 4 is shown with a straight distal end, it will be understood that various simple or compound curves could be formed in the distal end to enable the implant to be endoscopically or otherwise delivered to a variety of sites. An example of possible curves is shown in FIG. 20.

As shown in FIGS. 3 and 4, tissue anchor inserter 100 comprises a hollow handle 102, an elongated tubular shaft 104 extending from one end of the handle and having a distal end 106. End 106 is provided with a window 107 to enable a user to see the position of the anchor as will be understood below. The proximal end 108 of shaft 104 is secured to the distal end of handle 102 and communicates with the interior thereof. Handle 102 carries a pair of diametrically opposed trigger projections 110 and 112 which, as will be understood below, comprise the proximal end of a needle means 114. Handle 102 also carries a pusher handle 120 which, as will be understood below, is situated at the proximal end of a pusher means 122. The handle is also provided with a pair of finger recesses 124 and 126 to facilitate single handed operation.

As shown in FIGS. 5 through 10, needle means 114 comprises an elongated trocar or needle 130 extending distally from a slide body 131 to which trigger projection 110 is secured. In the preferred embodiment, needle 130 may be made of a stainless steel or a memory alloy such as nitinol and has a diameter of 0.025 inches (0.635 mm) to fit in anchor bore 13 which has a diameter of 0.026 inches (0.660 mm). Slide body 131 is formed of a suitable polymeric material which may be insert molded with needle 130. Slide body 131 is joined to the bottom of trigger 110 at a reduced-width neck portion 132, the purpose of which will be understood below. Trigger assembly 133 (FIG. 12) is formed by inserting slide body 131 into slide body 134 best seen in FIGS. 8–10. Slide body 134 is molded with trigger projection 112 and has a member 135 having a chamber 136 and a slot 137. Member 135 is joined to the bottom of trigger 112 at a reduced-width neck portion 138. Trigger assembly 133 is assembled with pusher means 122 shown in FIG. 11 by sliding the needle of body 131 into the lumen of pusher rod 142 and inserting body 131 into the chamber 136 of body 134, directing the needle through slot 137. This results in the trigger assembly being situated in the pusher body, as shown in FIG. 12.

Figure 13:
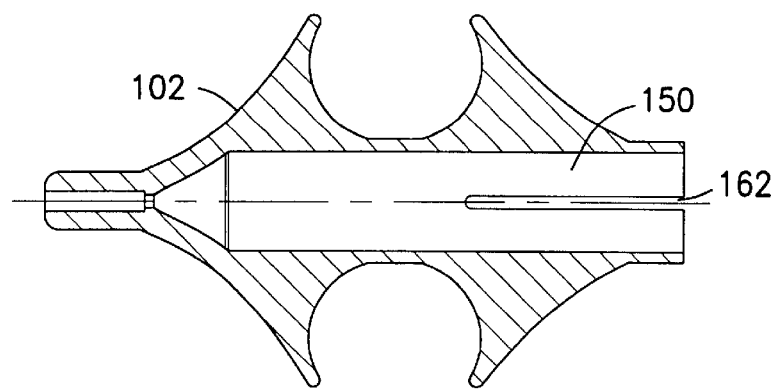
FIG. 13 is a plan view of the handle of the inserting instrument in cross-section.
Figure 26:
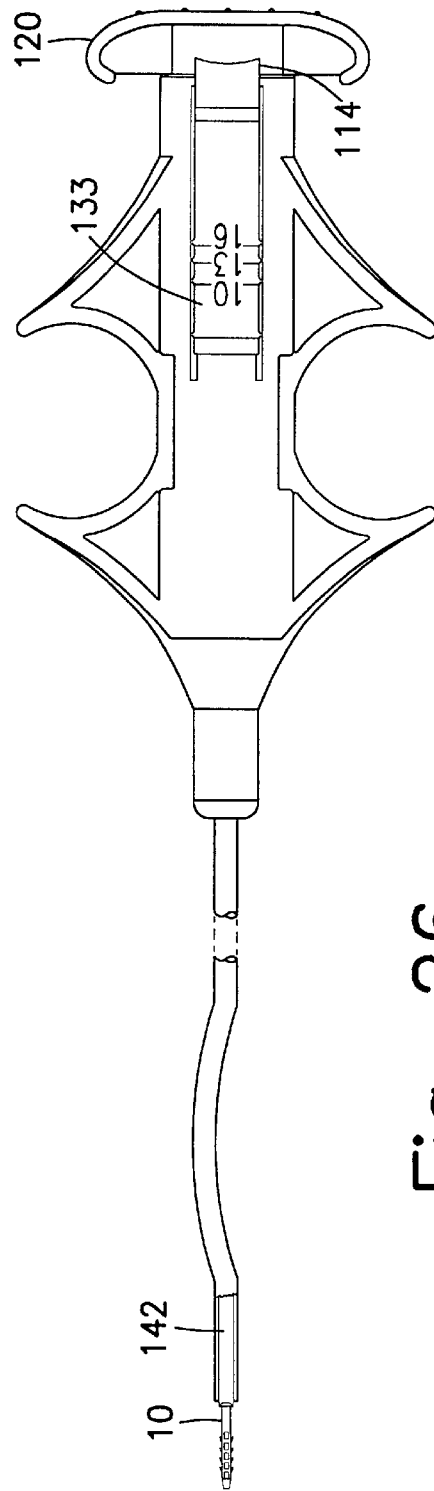
FIG. 26 shows another stage in the method of use.

As shown in FIG. 11, pusher means 122 comprises a body 140 having a pusher handle 120 at its proximal-most end and having an elongated cannulated pusher rod 142 extending from its distal end. Body 140 has an elongated slot 144 extending therethrough for receiving trigger assembly 133 and enabling the slide body to move proximally and distally within slot 144, independently of the motion of pusher body 140, between a proximal-most position as shown in FIGS. 3 and 4 and a distal-most position as shown in FIG. 26. If desired, only one trigger projection (110 or 112) may be utilized although the use of two symmetrical projections enables inserter 100 to be operated from either side of handle 102. (If only one trigger projection is utilized, slot 144 need not be a through-slot, but simply a recess in body 140.) Pusher body 140 is adapted to be slidably received within a receiving chamber 150 at the proximal end of handle 102 (best seen in FIG. 13) and may also be provided with a plurality of circumferentially arranged, outwardly extending projections 146. The projections rest against the rim 152 of chamber 150 and provide some resistance to the distal movement of pusher body 140 relative to handle 102 in order to prevent inadvertent delivery of the tissue anchor at the work site. The various lengths of shaft 104, needle 130 and pusher 142 rod are selected to facilitate the operation of the inserter using the method steps described below.

Figure 15:
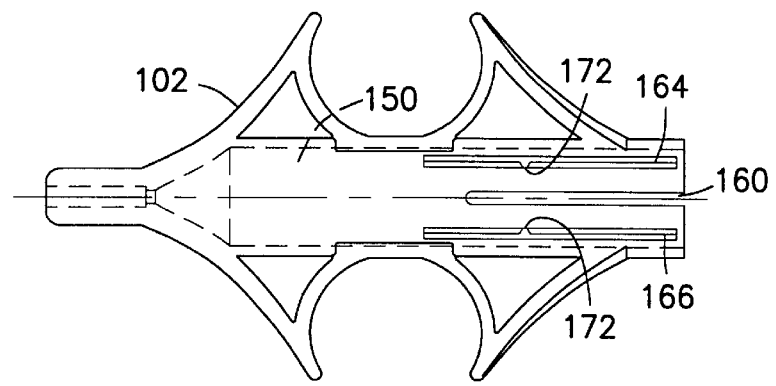
FIG. 15 is a plan view of the handle of the inserting instrument showing external features thereon.
Figure 16:
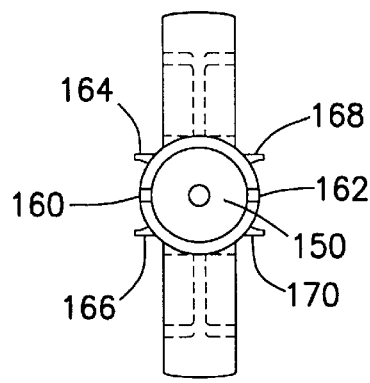
FIG. 16 is a right side view of FIG. 15.
Figure 14:
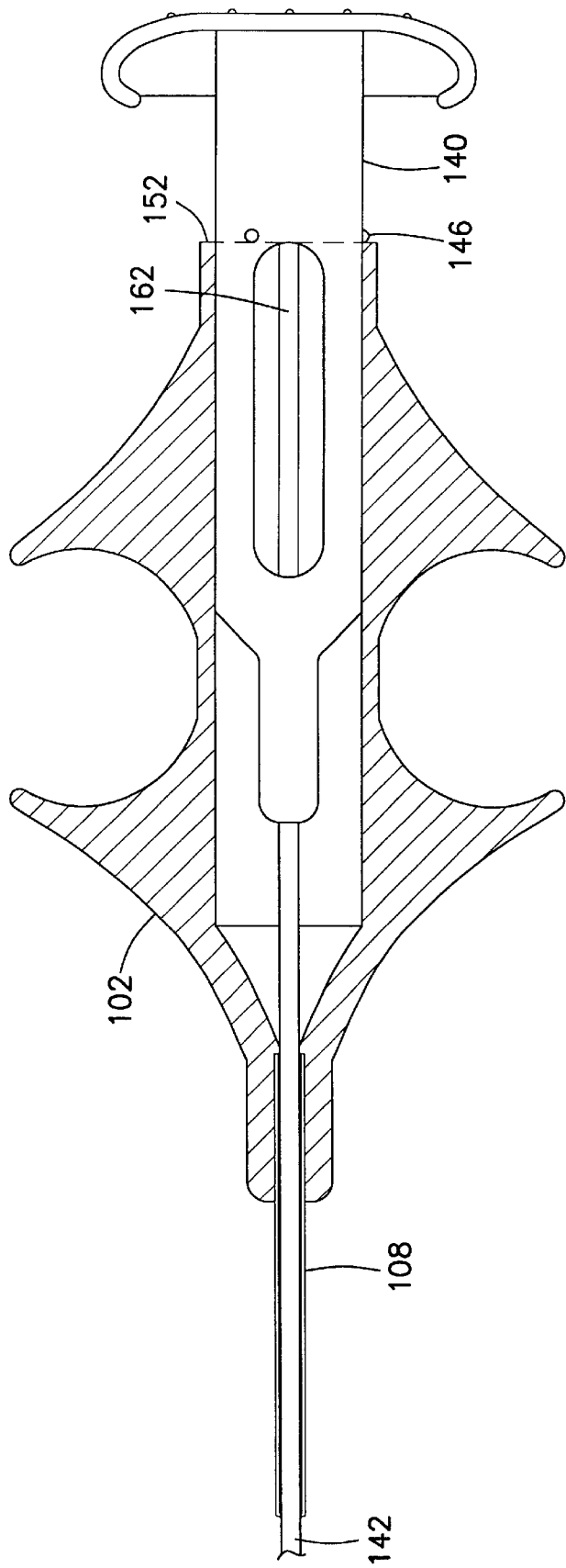
FIG. 14 is a plan view of the handle assembled with the proximal end of the pusher means.
Figure 17:
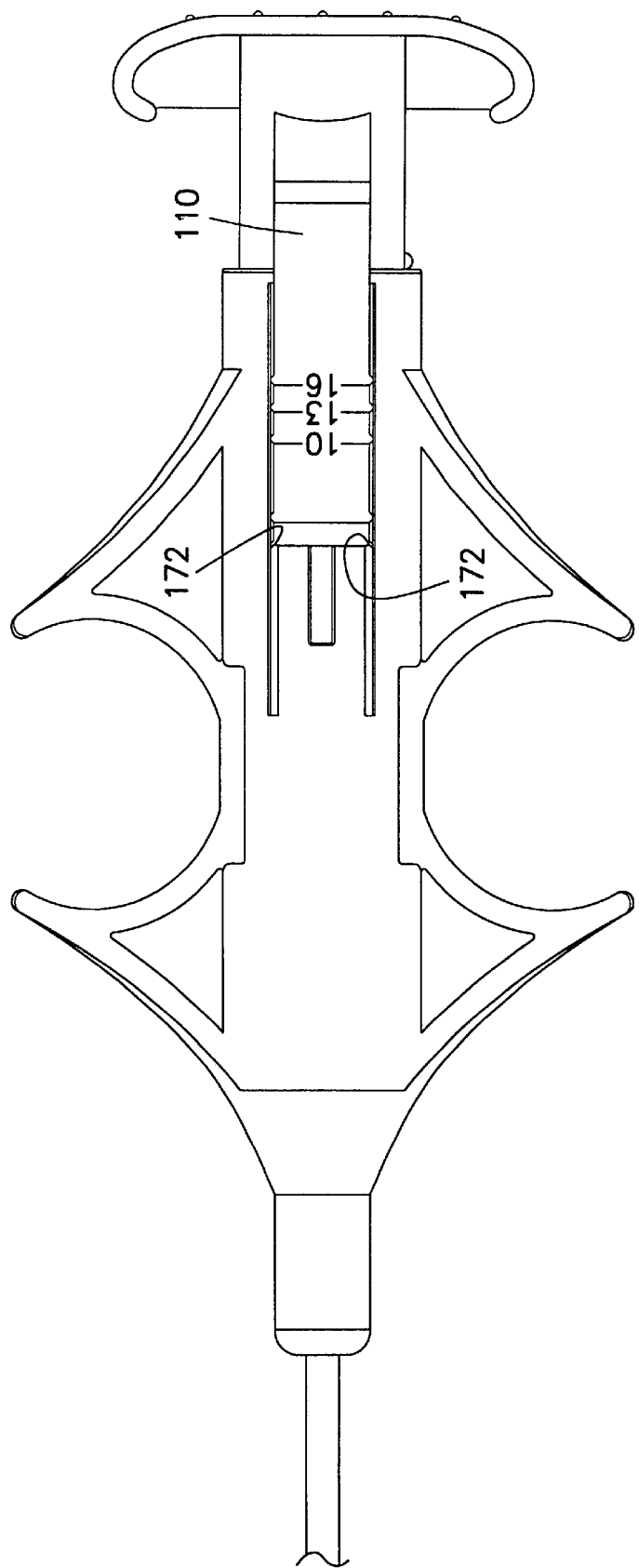
FIGS. 17–19 are plan views of the proximal end of the inserting instrument in various stages of use.
Figure 18:
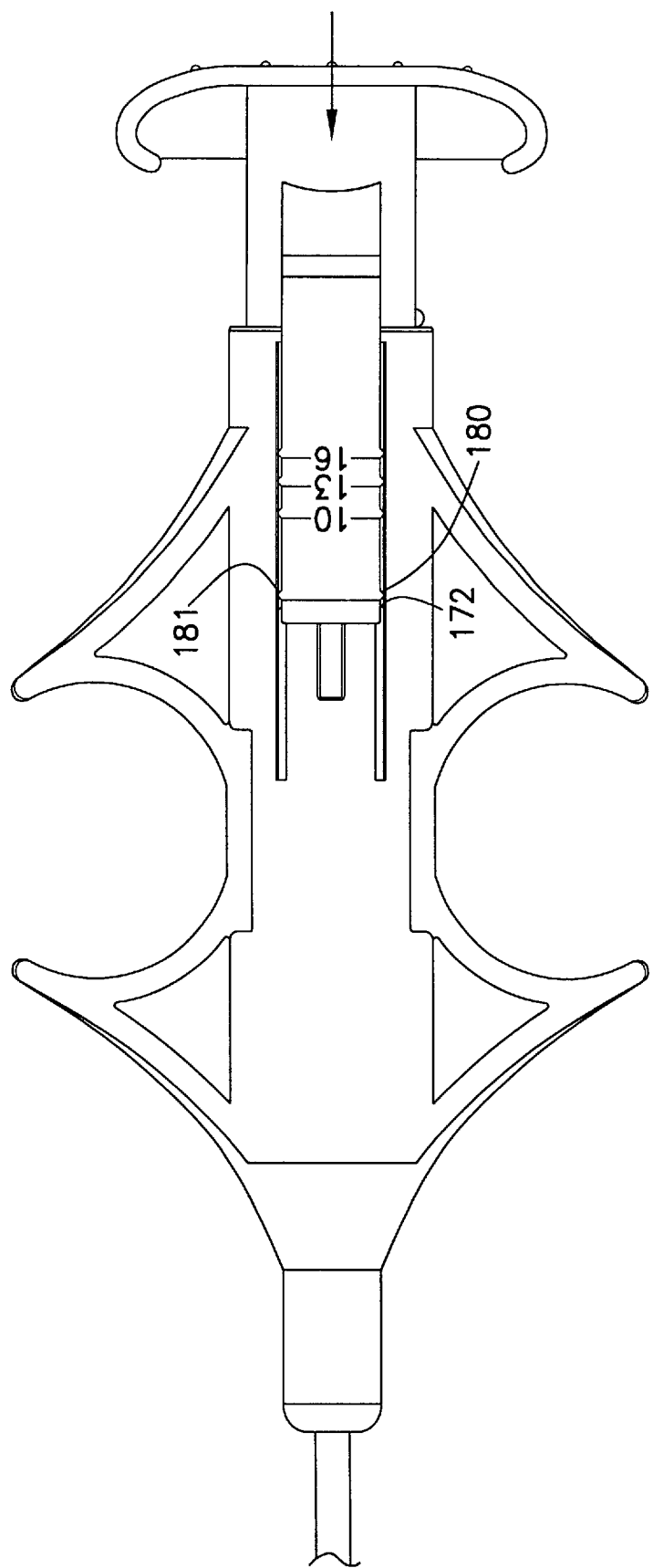
Figure 19:
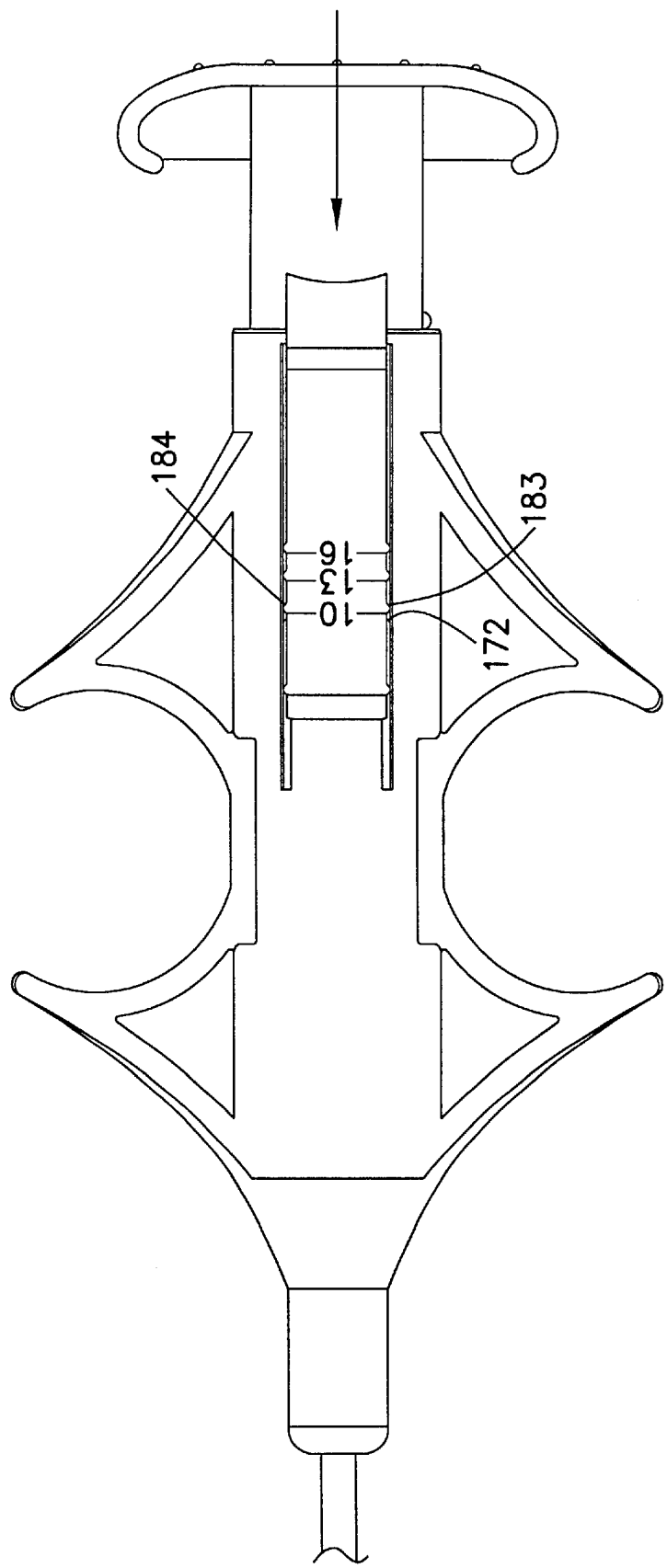

The body of handle 102 adjacent chamber 150 is provided with a pair of diametrically opposed slots 160 and 162 which receive neck portions 132 and 138, respectively. As shown in FIGS. 15 and 16, a pair of raised ribs 164 and 166 is parallel to slot 160 and a pair of raised ribs 168 and 170 is parallel to slot 162. Each rib has an inwardly extending projection 172 to provide a detent to a plurality of paired projections 174 molded into the bottom of trigger projections 110 and 112 (best seen in FIGS. 7 and 10). These projections comprise selective depth penetration means to enable a user to select the desired distance by which needle 130 extends beyond distal end 106. As shown in FIG. 17, when projections 172 are distal of any projections 174 on trigger 110 (or 112 since the projections are symmetrically situated), the needle will be understood to be totally within shaft 104. When projections 172 abut the distal-most projections 180, 181 as shown in FIG. 18, the needle will, in the preferred embodiment, be understood to extend 2 mm beyond end 106. As shown in FIG. 19, when projections 172 abut projections 183, 184 the needle will, in the preferred embodiment, be understood to extend the distance indicated by the indicia, here shown as 10 mm. Additional detents are provided at 13 mm and 16 mm as shown, the various marked distances corresponding to lengths of the tissue anchor to be implanted. The projections further serve to provide tactile and audible feedback to the surgeon to facilitate use and operation of the inserter.

Referring now to FIGS. 20 through 27, the single-handed method of using the insertion instrument to insert a cannulated tissue anchor will be described. As shown in FIG. 20, the first step in the process is to move needle means 114 distally in order to extend needle 130 from the distal end 106. The movement of needle means 114 is limited by virtue of the dimensions of the various components of the device so that the needle 130 will extend beyond the distal end 106 a selected distance equal to the length of the tissue anchor for which the system is being used (e.g. 10 mm, 13 mm or 16 mm). In FIG. 20 the trigger assembly 133 is at the 16 mm mark. The next step in the process is to load a tissue anchor 10 onto the protruding needle by inserting the needle through the central bore of the anchor (FIG. 21). In FIG. 21 the trigger assembly 133 is at the 13 mm mark and the anchor shown is 13 mm long. The process described in these drawings is applicable to all anchor sizes. As shown in FIG. 22, needle means 114 is then retracted to its proximal-most position in order to retract the needle and the anchor into tube 106. The distal end of the tissue anchor/inserter assembly in this loaded condition is shown in greater detail in FIG. 23 which, for clarity, is not to scale (in the preferred embodiment the dimensions of the anchor and the various tubes and rods may clearly be made to create a tighter fit). It will be noted that in this loaded configuration the anchor resides in an annular chamber 190 at the distal end of inserter 100 and the proximal side of head 30 of the tissue anchor abuts the distal tip of pusher rod 142. The assembled anchor/inserter is now ready for insertion into the patient and advancement of the distal end 106 to the work site.

Figure 24:
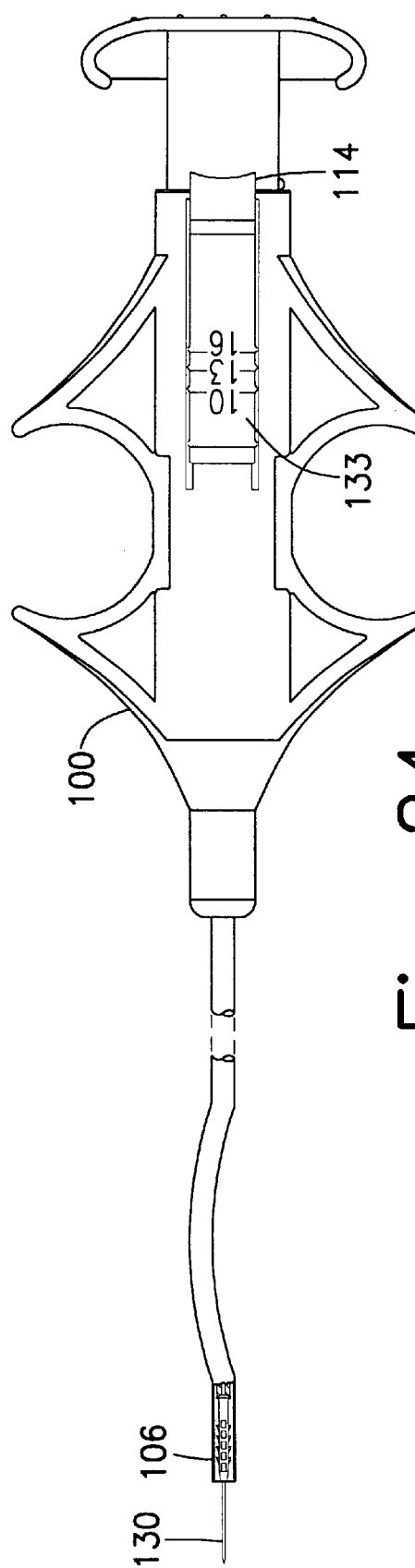
FIG. 24 shows the instrument in a different stage of the method of use.
Figure 25:
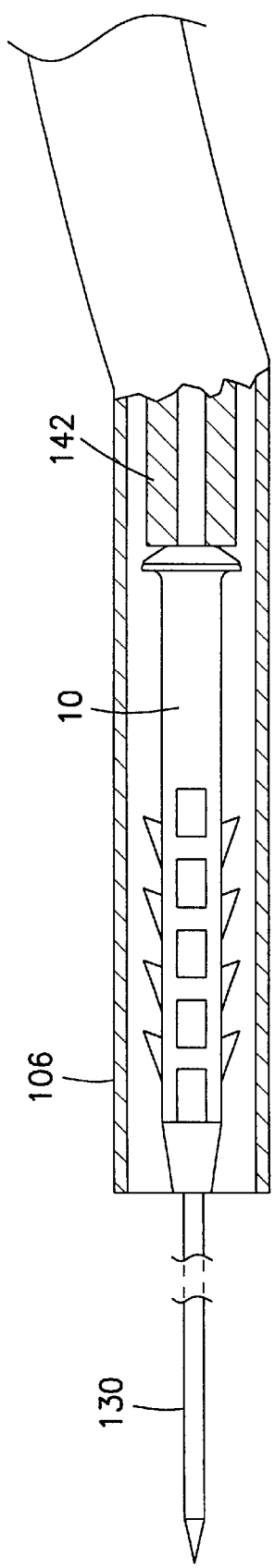
FIG. 25 is a close up of the distal end of FIG. 24.

When the anchor is ready to be inserted, the distal end 106 is placed as desired and needle means 114 is pushed distally the desired distance (e.g. 13 mm as shown in FIGS. 24 and 25) in order to advance needle 130 into the tissue to be repaired (not shown). The needle would normally extend across a tear in tissue (such as meniscus) and the tissue anchor would be placed to close the tear and hold the tissue together. The needle is sized to slide easily within the bore of the anchor so it can be advanced and properly positioned before the anchor is pushed in. Once the needle 130 is sufficiently extended, pusher 120 may be pushed distally as shown in FIGS. 26 and 27 thereby causing pusher rod 142 to push anchor 10 along needle 130 into the tissue. The progress and position of the anchor may be seen through window 107 (best seen in FIG. 3). The pusher rod may be made to extend slightly beyond the distal tip of end 106 in order to "countersink" the head of the tissue anchor into the tissue. In the preferred embodiment of the inserter described above, the pusher rod extends 1 mm beyond the distal tip of shaft 104, as shown at 143, at all of the trigger positions. That is, for example, in the 16 mm position the needle extends 15 mm beyond the pusher rod which extends 1 mm beyond the tip. The instrument may be removed after retracting the needle from the site.

The method of operation of inserter 100 may be accomplished in other embodiments. For example, a pistol grip handle (not shown) may be provided with a trigger activated two-part slide with predetermined stops such that one squeeze of the trigger would engage it with the (proximal end of the) needle and cause the needle to be pushed distally, release of the trigger would disengage it from the needle and a second squeeze would engage it with the (proximal end of the) pusher rod and cause it to be pushed distally, thus pushing the anchor out of a sheath attached to the handle and encasing the anchor, needle and pusher. Alternatively, separate triggers could be provided for the needle and the pusher.

While the method described above can be initiated by the manual loading of a cannulated tissue anchor onto the needle of the insertion device, the tissue anchor may alternatively be held in a combination package and loading device which facilitates the assembly of the anchor with the insertion device. Such a package/loading device is shown in FIGS. 28 through 36.

Figure 28:
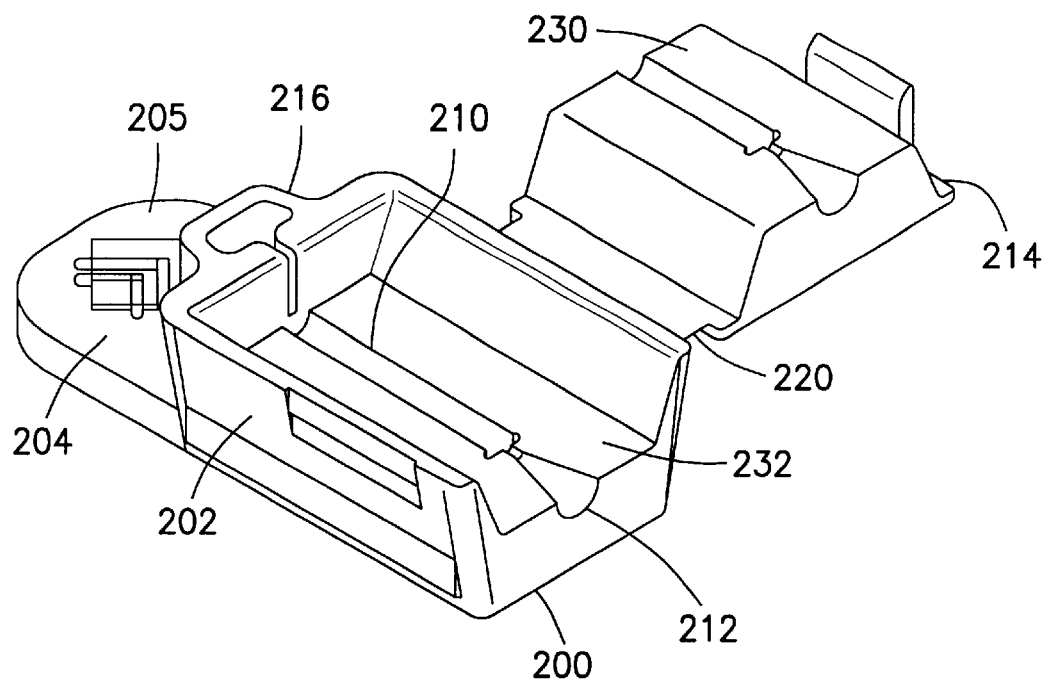
FIG. 28 is a front perspective view of a molded device used in assembling a cannulated tissue anchor onto an inserting instrument such as that shown in FIG. 3, the package/loading device being shown in an open configuration.

As shown in FIG. 28, package/loading device 200 comprises a receptacle portion 202 and a holding portion 204, and serves as a biocompatible package for holding and shipping the tissue anchor after its manufacture and a loading fixture for use with an inserter. The package can also hold the anchor during its sterilization by conventional means. All parts of the device may be integrally molded, sterilizable and, if desired, translucent or transparent. Receptacle 202 comprises a tissue anchor receiving means 210, a funnel means 212 and a hinged cover 214. Receptacle portion 202 is situated adjacent a protection/gauge means 216, the purpose of which will be understood more fully below.

Holding portion 204 comprises a flat finger grip area 205. The lateral sides 217 and 218 of receptacle portion 202 comprise additional finger grip areas. All such areas may be provided with anti-slip ridges 219 or other structures to enhance a user's manipulation of the package.

Figure 29:
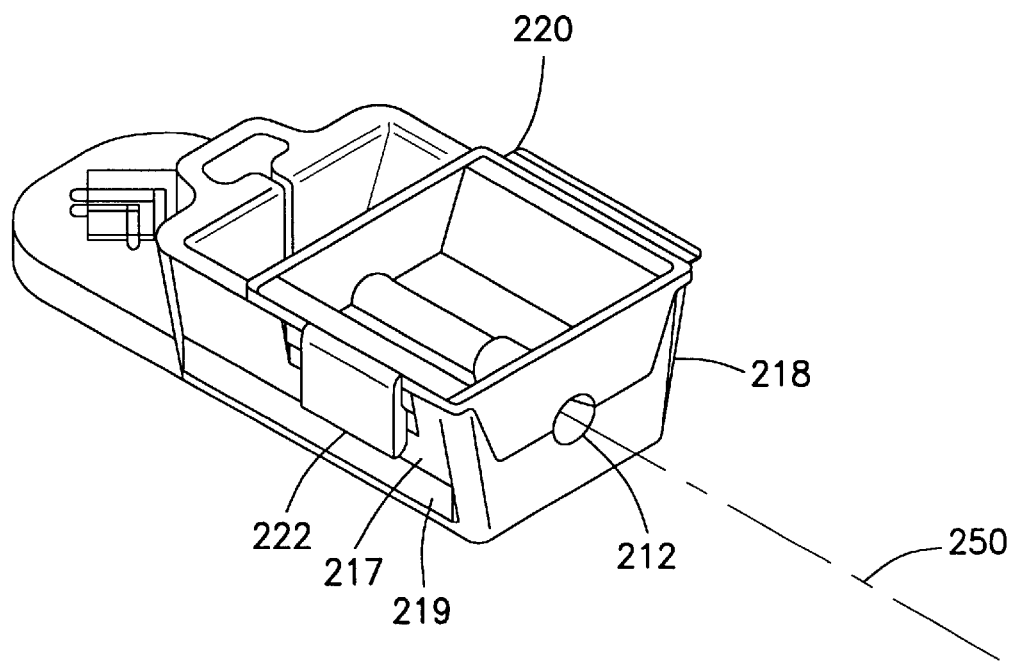
FIG. 29 is a front perspective view of the loading device of FIG. 28 shown in a closed configuration.

As shown in FIG. 29, cover 214 may be moved about its hinge 220 into a closed position and retained there by a latch means 222. Cover 214 and receptacle 202 have surfaces 230 and 232, respectively which are intended to produce a receiving space between them within which tissue anchor 10 is to be retained. Surfaces 230 and 232 are provided with complementary recesses which form anchor retaining means 210 and funnel means 212 when the cover is closed. In the closed position, funnel means 212 presents a circular opening at the proximal end of the loading device in order to facilitate assembly of the anchor with the inserter 100 as will be understood below. Funnel means 212 provides a conical docking feature to help a user aim the needle into the bore of the device which is held in alignment with the axis of the funnel.

Figure 30:
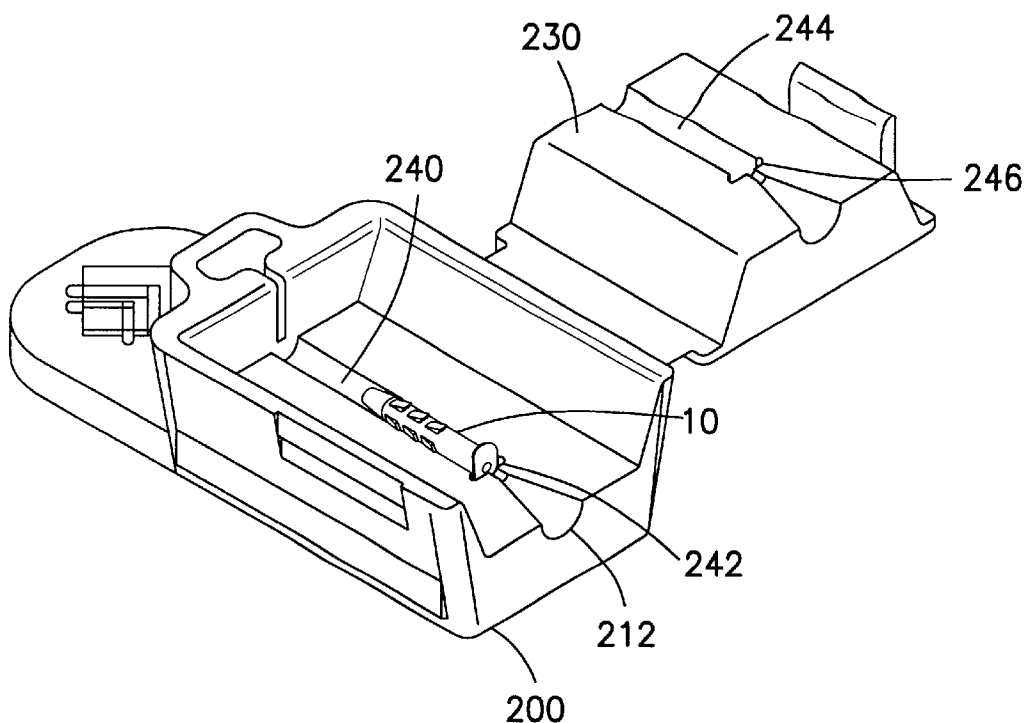
FIG. 30 is a view of the loading device of FIG. 28 showing a cannulated tissue anchor positioned within the device prior to it being closed.
Figure 31:
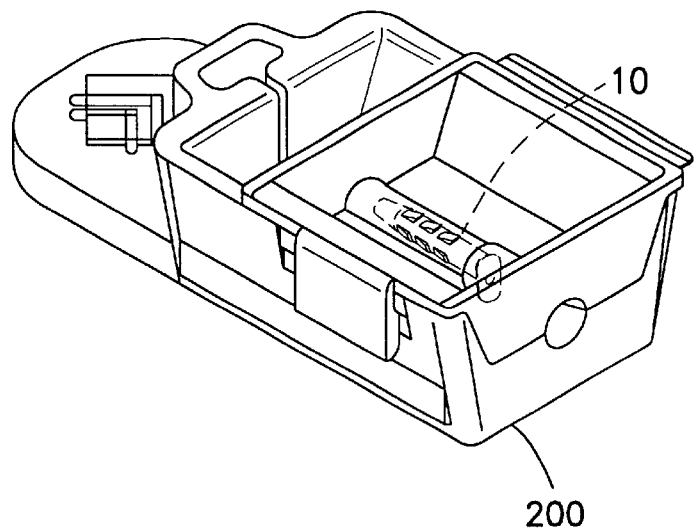
FIG. 31 is a front perspective view of the loading device of FIG. 20 shown in a closed configuration.

As shown in FIG. 30, a cannulated tissue anchor 10 may be placed in tissue anchor receiving means 210 with the body of the anchor in trough 240 and the head of the anchor in transverse recess 242, both trough 240 and recess 242 being axially aligned with funnel means 212. Trough 240 and recess 242 have symmetrical counterparts 244 and 246, respectively, formed in surface 230 of cover 214. When the cover is closed, the tissue anchor is retained firmly within tissue anchor retaining means 210 with its axially aligned bore aligned with the axis 250 of funnel means 212. FIG. 31 shows a view of a closed, transparent loading device retaining a tissue anchor therein. It will be understood that the angular orientation of the major axis of the head of anchor 10 may or may not be fixed relative to other components of the package and inserter.

Figure 32:
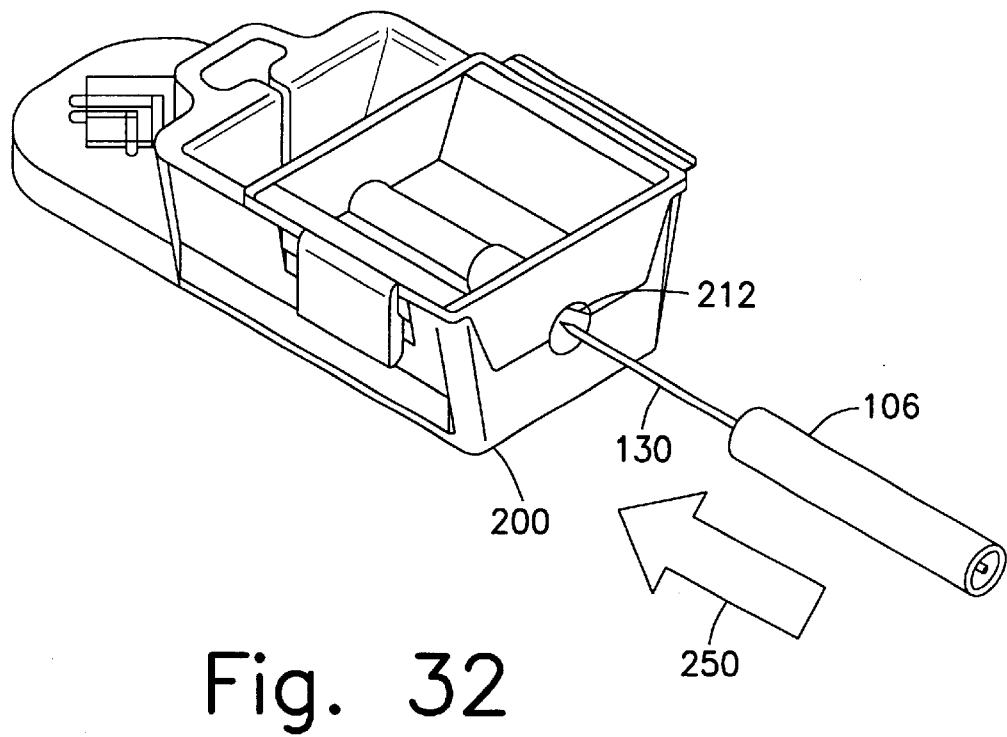
Figure 33:
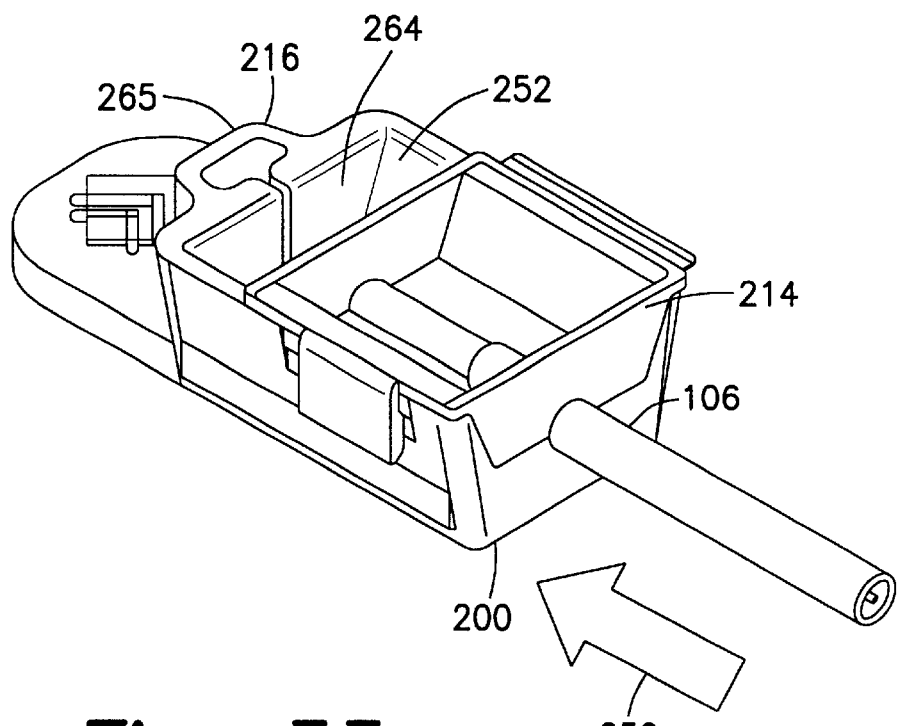
Figure 34:
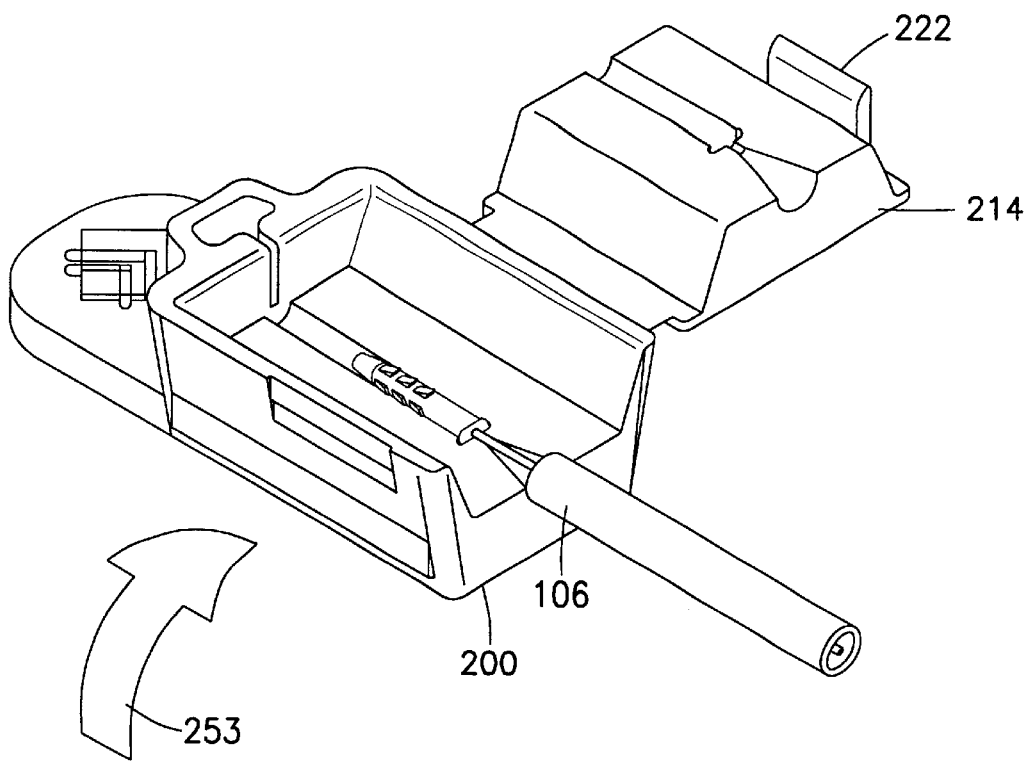
Figure 35:
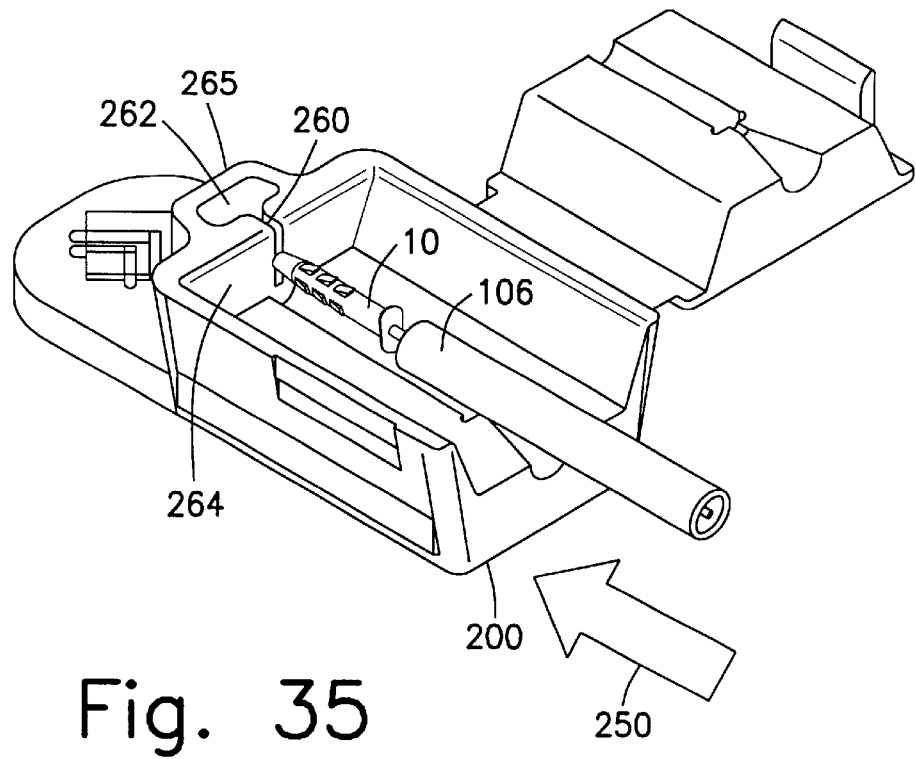

The steps of using the loading device 200 to assemble the cannulated tissue anchor with the insertion device 100 are shown in FIGS. 32 through 36. For simplicity, only the distal end 106 of the insertion device and the distal end of needle 130 are shown. As shown in FIG. 32, needle 130 is extended beyond the distal end 106 and the insertion device is moved in the direction of arrow 250 in order to enable the funnel means 212 to guide the tip of needle 130 into the axial bore of the cannulated tissue anchor. The inserter is advanced distally until the position shown in FIG. 33 where distal end 106 either abuts or is close to abutting the proximal side of the closed loading device at which point the needle will be situated within the axial bore of the tissue anchor. Depending upon the length of the needle and anchor, the distal tip of the needle may be visible in the space 252 between cover 214 and end wall 264. As shown in FIG. 34, cover 214 may be opened in the direction shown by arrow 253 by releasing latch 222 thereby releasing the anchor. As shown in FIG. 35, the distal end 106 of the inserter may then be moved further in direction 250 in order to enable the distal tip of needle 130 to pass through slot 260 into protection/gauge means 216 which includes a receiving chamber 262 formed between end wall 264 and blocking or protective wall 265. Slot 260 is an aperture sized to receive the needle while preventing advancement of the anchor beyond end wall 264, thereby enabling the anchor to be fully seated onto needle 130. In the preferred embodiment, the width of slot 260 is 0.026 inches (0.660 mm). End wall 264 simply serves to define slot 260 while protective wall 265 serves as protection against inadvertent user contact with the tip of the needle. Further advancement of distal end 106 as shown in FIG. 36 will enable the anchor to be pushed into the interior of the distal end. This alone will tend to move the trigger means 114 distally although the trigger means may be simultaneously moved distally by a user to facilitate the placement of the anchor within the interior of the distal end of the insertion device. The insertion device may now be used in the manner described above with respect to FIGS. 24 through 27.

While the inserter 100 has a trigger position which defines when the needle extends 2 mm beyond the distal end of the instrument, other methods may be used to so position the needle. For example, the thickness of wall 264 may serve as a gauge to indicate the desired distance by which the tip of the needle extends beyond the tip of the anchor. As the needle extends through slot 260 and the end 106 abuts wall 264, the user may see the needle in chamber 262. If desired, by retracting the needle so it extends from end 106 only by the thickness of wall 264 (e.g. 2 mm), the user can elect to have the needle extend a given amount (to aid in tissue manipulation, for example, prior to piercing the tissue in preparation for anchor placement).

It will be understood by those skilled in the art that numerous improvements and modifications may be made to the preferred embodiment of the invention disclosed herein without departing from the spirit and scope thereof.

What is claimed is:

1. A package for retaining a cannulated tissue anchor having a bore comprising:

a base having a first, bottom surface for receiving a cannulated tissue anchor thereon in predetermined orientation;

movable holding means having a second, top surface, opposed to said first, bottom surface, for holding the cannulated tissue anchor adjacent said first, bottom surface of said base; and conical funnel means for being aligned with a cannulated tissue anchor held between said first and second surfaces, said funnel means for facilitating insertion of an elongated member into the bore of the cannulated tissue anchor.

2. A package according to claim 1 further comprising:

cooperating trough means on each of said first and second surfaces for retaining the cannulated tissue anchor.

3. A package according to claim 1 further comprising:

receiving means situated distally of said funnel means and axially aligned therewith for receiving therein said elongated member after it has passed through said bore.

4. A package according to claim 1 wherein said base, said movable holding means and said funnel means are integrally formed together.

5. A package according to claim 3 wherein said receiving means is an aperture through which said elongated member may pass.

6. A package according to claim 5 further comprising a protective wall means, situated distally of said receiving means, for preventing said elongated member from extending beyond a predetermined point.

* * * * *